United States Patent [19]

Hamada et al.

[11] 4,234,306
[45] Nov. 18, 1980

[54] METHOD AND APPARATUS FOR SENSING JAW POSITION AND MOVEMENTS AND UTILIZING SENSED DATA

[75] Inventors: James H. Hamada, Los Altos; Jeffrey R. Bender; Earl T. Price, both of San Jose, all of Calif.; Dennis A. Ingebretsen, Oakton, Va.

[73] Assignee: HBTI, San Jose, Calif.

[21] Appl. No.: 58,689

[22] Filed: Jul. 18, 1979

[51] Int. Cl.³ ............................................. A61C 11/02
[52] U.S. Cl. ................................................... 433/55
[58] Field of Search .................. 128/782, 303 B, 777; 433/54, 55, 68, 69, 196

[56] References Cited

U.S. PATENT DOCUMENTS

| | | | |
|---|---|---|---|
| 1,664,210 | 3/1928 | Hall | 128/782 |
| 3,321,832 | 5/1967 | Weisberg | 433/55 |
| 3,712,716 | 1/1973 | Cornsweet | 128/782 |
| 3,717,857 | 2/1973 | Evans | 128/782 |

FOREIGN PATENT DOCUMENTS

1931004  1/1970  Fed. Rep. of Germany .......... 128/777

Primary Examiner—Robert Peshock
Attorney, Agent, or Firm—Victor R. Beckman

[57] ABSTRACT

Method and apparatus for sensing jaw position and movements and for converting the sensed data to dental articulator settings for simulating said movement are disclosed. Included are a pair of clutches which are fitted to the patient's maxillary and mandibular teeth. The respective clutch plates are removably secured to the housing of a jaw movement recording device and to a movable indicia-bearing arm. At least three indicia are mounted at the inner end of the arm in a manner such that they are viewable from three mutually orthogonal directions. Photoresponsive means are included for sensing and/or recording the indicia during and/or following displacement of the indicia-bearing arm during and/or following condyle movements of the patient's mandible. By this means, information as to the position and skew angle of the indicia in three dimensions is provided. This information, together with measurements relating the hinge axis of the patient's jaws to the device, is used for determining border positions and/or movements of the right and left mandibular condyles during jaw movement, and dental articulator settings required to reproduce such movements. A properly programmed digital computer may be used for making such determinations.

21 Claims, 17 Drawing Figures

FIG-5A  LEFT LATERAL

FIG-5B  RIGHT LATERAL

FIG-5C  PROTRUSIVE

FIG-5D  COMPOSITE

METHOD AND APPARATUS FOR SENSING JAW POSITION AND MOVEMENTS AND UTILIZING SENSED DATA

BACKGROUND OF THE INVENTION

Numerous arrangements are known for sensing and/or recording jaw movements for use in establishing setting for adjustable dental articulators required to simulate such movements. With many arrangements the device is useable only with a particular type of articulator, and not with others. One such mandible movement recorder includes mechanical pantographs which are used directly with the articulator for adjusting the same. Not only does the use of such arrangement require extensive training and experience, but individual technique and judgement are required on the part of the operator performing both the initial pantograph mandibular reading and transfer of the pantograph data to the articulator. As a result, the final articulator adjustments may vary greatly on a single patient from operator to operator, or between multiple measurements conducted by the same operator. Additionally, once the pantograph has been adjusted to an individual patient it cannot be used with additional patients until completing the process of duplicating the pantograph readings on the mechanical articulator. Since this process may require several hours per patient, the usefulness of the device is impaired when many patients are involved.

SUMMARY OF THE INVENTION

An object of this invention is the provision of method and apparatus for sensing and/or recording a patient's mandibular movements to provide information from which movements of the patient's mandible condyles may be obtained as well as articulator settings required for adjusting an articulator to simulate said movements, which avoid the above-mentioned and other short-comings of prior art arrangements used for this purpose.

An object of this invention is the provision of improved method and apparatus for obtaining jaw movement information from a patient which are highly accurate yet require a minimum of operator skill.

An object of this invention is the provision of improved method and apparatus for obtaining a record of a patient's mandibular movements and for converting the same to information of actual right and left mandibular condyle movements from which information articular settings for any of a variety of articulators may be obtained for use in simulating said condyle movements.

The above and other objects and advantages of this invention are achieved by use of jaw movement sensing means which includes a fixed member and a freely movable indicia-bearing arm. Clutches are fitted to the patient's teeth and attached to the fixed member and outer free end of the indicia-bearing arm for movement of the arm, with respect to the fixed member, when the patient's jaws are worked. Incidia at the inner end of the movable arm are viewable from along three mutually orthogonal directions. The position of the indicia is sensed and/or recorded by use of photoresponsive means, such as photographic film, to provide a tracing, or record, of the patient's mandibular movements and/or border movement positions. Information from the tracing or record together with physical dimensions relating the apparatus to the patient's hinge axis, is used for computation of actual mandibular condyle movements and dental articulator settings required to simulate such movements. A printout of articulator settings, for the particular type articulator to be used, may be provided.

BRIEF DESCRIPTION OF THE DRAWINGS

The invention will be better understood from the following description when considered with the accompanying drawings. In the drawings, wherein like reference characters refer to the same parts in the several views.

Figure 1:
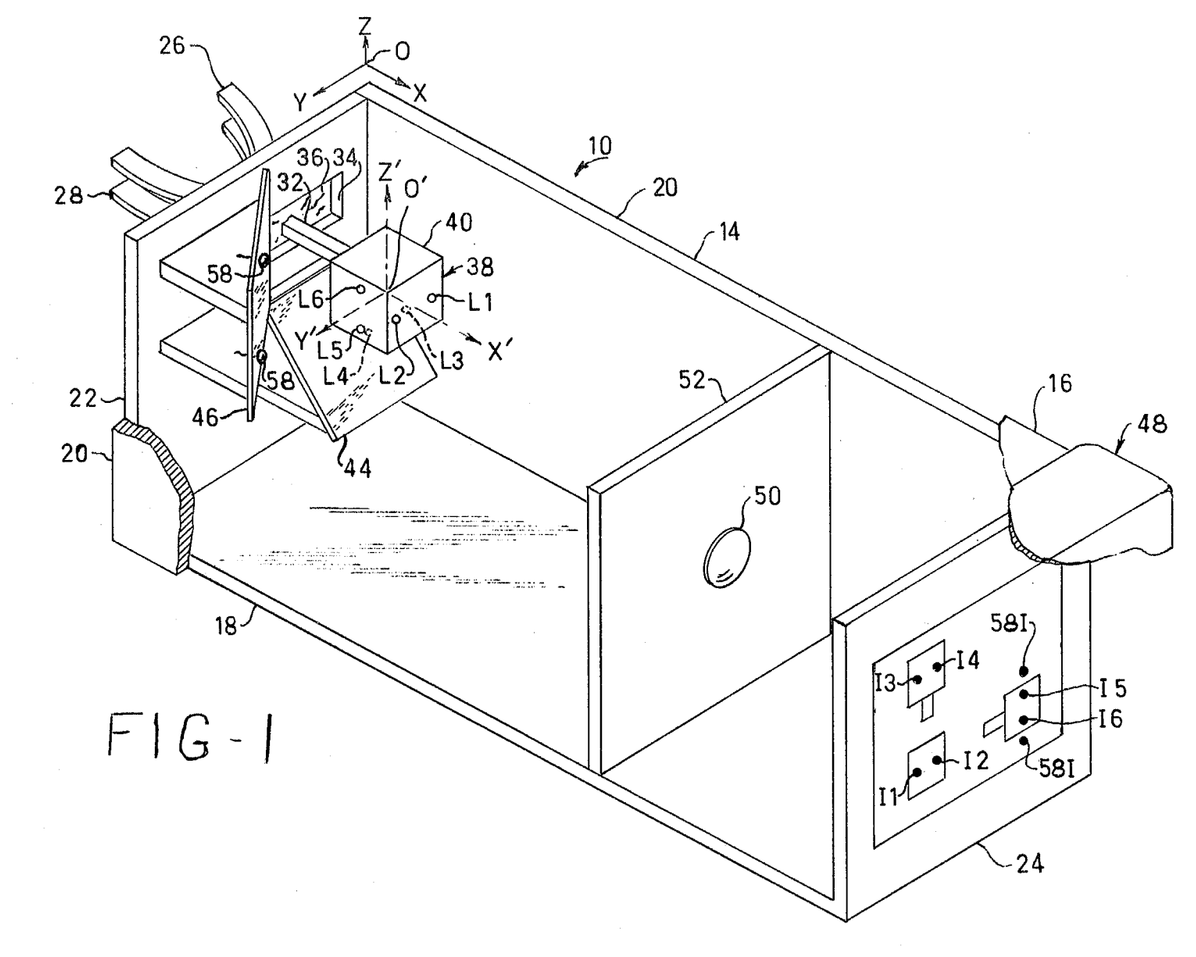
FIG. 1 is a perspective view, with parts shown broken away for clarity, of a mandibular movement recording system which embodies the present invention.
Figures 2, 3, 4:
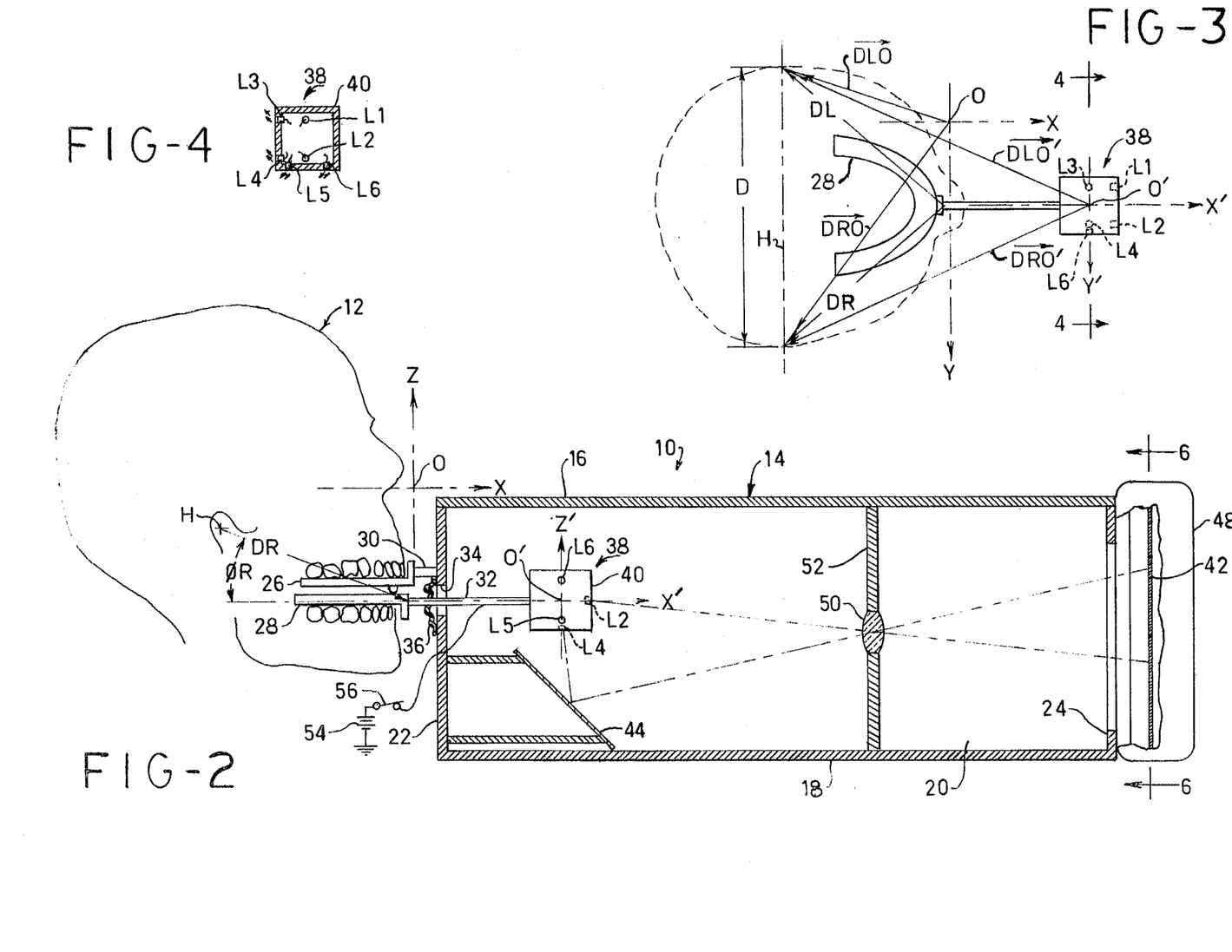
FIG. 2 is a longitudinal sectional view of the system shown in FIG. 1 and illustrating the use thereof with a patient.
FIG. 3 is a plan view of the movable light supporting arm included in the recording system and showing measured quantities relative to a patient used in the practice of this invention.
FIG. 4 is a cross-sectional view of the light source means taken along line 4—4 of FIG. 3.

Reference first is made to FIGS. 1 and 2 wherein a novel mandibular movement recording device 10 is shown for obtaining a measure of the movement of the mandible, or lower jaw, relative to the maxilla, or upper jaw, of the patient 12 (FIG. 2). The device comprises a housing 14 which includes top and bottom members 16 and 18, respectively, opposite side walls 20, and front and rear walls 22 and 24, respectively. The top preferably is removably attached to the side and end walls for access to components within the housing, Also, in the illustrated arrangement light-tight joints are provided to prevent ambient light from entering the housing therethrough.

Upper and lower clutches 26 and 28, shown in simplified form in the drawings, are fitted to the maxillary and mandibular teeth, respectively, of the patient 12. The upper clutch 26 is removable secured to the front wall 22 through an interconnecting arm 30 for rigid attachment of the maxillary teeth to the housing. The lower clutch 28 is removably attached to the outer free end of a movable, indicia-bearing, arm 32 extending through an aperture 34 formed in the front wall 22 of the housing. A flexible member 36 at the opening 34 provides a light-tight seal between the arm 32 and front wall 22 while allowing for six degrees of freedom of movement of the arm during jaw movement; that is, the arm 32 is positionable in 3 dimensions and is angularly rotatable in 3 dimensions.

The inner end of the arm 32, located inside the housing 14, provides a movable reference frame identified by mutually orthogonal axes X', Y' and Z' at origin O', the position and skew angle of which frame, relative to a fixed reference frame identified by mutually orthogonal axes X, Y, and Z at origin O, is recorded during jaw movements. The location of the fixed reference frame (i.e. fixed relative to the housing 14) is chosen for convenience, and in the illustrated arrangement the frame position is selected such that the front surface of the upper clutch 26 lies in the Y, Z plane thereof.

The inner end of the movable indicia-bearing arm 32 is provided with indicia by means of which the three-axis position of the arm and the three space, or skew, angles thereof relative to the housing may be established. For purposes of illustration, and not by way of limitation, the indicia in the FIG. 1-4 arrangement comprise light source means 38 which includes a plurality of point light sources L1, L2, L3, L4, L5 and L6. The point light sources, which may be of any suitable type, such as light-emitting diodes (LEDs), or the like, are shown carried by a light support, or housing, 40 affixed to the inner end of arm 32. The light source indicia are arranged in pairs at three sides of the light housing 40, with pairs L1 and L2, L3 and L4, and L5 and L6 being viewable from points along only the X', Z' and Y' axes, respectively, of the movable reference coordinate system, without being viewable from along the other two axes thereof. Also, for reasons which will become apparent hereinbelow, the pairs of light sources preferably are located equal distances from their associated axes and equal distances from the origin O' of the movable reference frame. In FIG. 4, the light sources L1–L6 are shown located at recessed positions within apertures in the walls of the light support housing 40 to prevent direct viewing of light therefrom at positions except along directions extending from the faces of the LEDs.

Information concerning the spacial position of the moving reference coordinate system relative to the fixed coordinate system is obtained by viewing the indicia from three mutually orthogonal planes parallel to the YZ, XY and XZ planes of the fixed reference frame at the front, side and bottom, respectively, of the light source means 38. To facilitate sensing and recording at a single light responsive means 42, light from two pairs of point light sources, namely L3 and L4, and L5 and L6, are reflected by front surface mirrors 44 and 46, respectively, adjacent the bottom and side of the light source means, and onto the light responsive means 42. In the FIG. 1-4 arrangement the light responsive means 42 comprises photographic negative film contained in a film pack 48 removably attached by means not shown to the rear housing wall 24. The film negative may be included in a Polaroid type film pack for immediate developing and printing of exposed negatives. A focusing lens, or lens system, 50 carried by an opaque wall 52 serves to focus light from the point light sources L1 through L6 onto the light responsive means 42. It will be apparent that the lens 52 and film negative 42, together with associated components comprise, essentially a camera for recording light tracings provided by movement of the light source means 38. The camera may include a shutter, not shown, for light control.

Figure 5A:
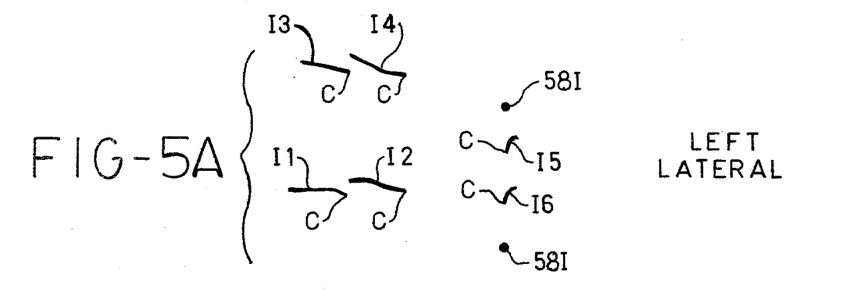
FIGS. 5A, 5B, 5C and 5D show light tracings at the focal plane of the optical system included in the recording system produced during various mandibular movements of the patient.
Figure 5B:
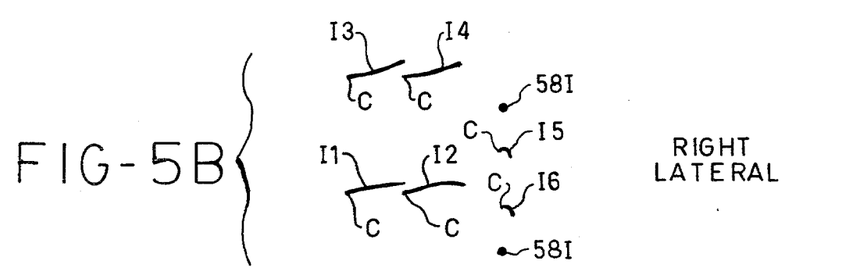
Figure 5C:
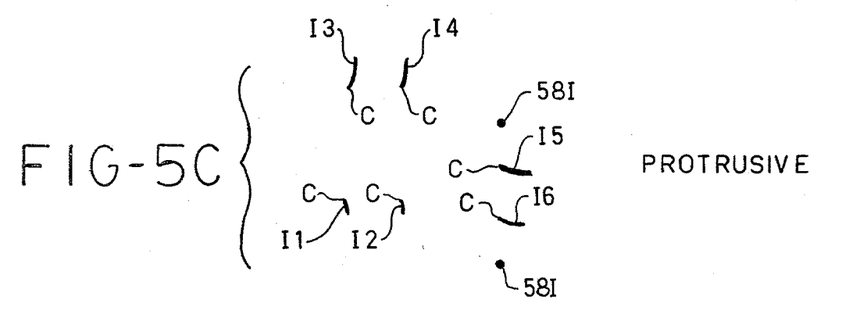

As diagrammatically illustrated in FIG. 2, the light sources L1 through L6 are adapted for simultaneous energization by connection thereof to a power source 54 through a switch 56. When the switch 56 is closed by the operator the light sources are simultaneously energized and the relative positions thereof recorded on the negative film 42. In FIGS. 5A through 5C traces of the light images I1 through I6 at the focal plane of the system are shown for left and right lateral and protrusive jaw movements, respectively, and in FIG. 5D composite traces for the three movements are shown. In these drawings, light source positions with the mandible in centric are identified by reference character C.

Figure 6:
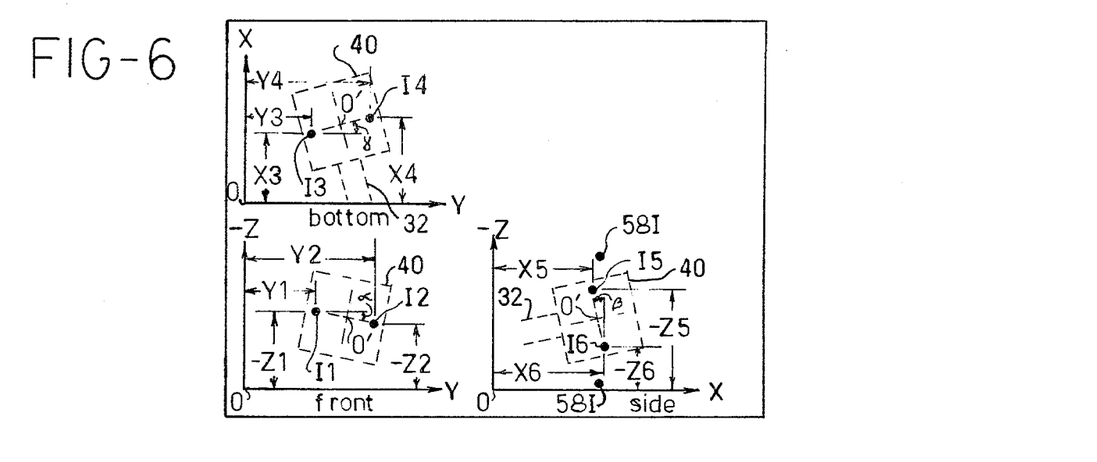
FIG. 6 is a diagrammatic view at the focal plane of the optical system taken along line 6—6 of FIG. 2 used to illustrate calculation in three dimensions of the position and skew angle of the light source means relative to the housing.

For an understanding of how the light image tracings may be used to determine the position and skew angle of the light source means 38 at the end of the movable arm 32 relative to the housing 14, reference is made to FIG. 6. There, the light images I1 through I6 are shown for a given relative position of the jaws, say, during right lateral movement thereof. Images of the X, Y and Z axes of the fixed reference frame together with broken line showings of the light-source housing 40 and fragmentary portions of the attached arm 32, are shown in FIG. 6 to facilitate an understanding of the invention. Also, the front, bottom and side views of the light source means are labelled such for convenience.

As viewed from the front, bottom and side, the origin O' of the movable reference frame is located at the midpoint of each of the light source image pairs I1 and I2, I3 and I4, and I5 and I6, respectively. In FIG. 6 measurements X3 and X4 at the bottom view, Y1 and Y2 at the front view, and Z5 and Z6 at the side view, are shown from which the origin O' of the movable reference frame relative to the fixed reference frame is given as folllows:

$$XO'=(X3+X4)/2 \qquad (1)$$

$$YO'=(Y1+Y2)/2 \qquad (2)$$

$$ZO'=((-Z5)+(-Z6))/2 \qquad (3)$$

It here will be apparent that positions XO', YO' and ZO' also may be obtained from measurements made to the illustrated X, Y, and Z axes from images I5 and I6, I3 and I4, and I1 and I2, respectively, if desired.

The illustrated angles $\alpha$, $\beta$ and $\gamma$ between the fixed and movable reference frames are calculated by solving the right triangles formed by each pair of light images in the fixed coordinate system as follows:

$$\alpha = \tan^{-1}[(Z1-Z2)/(Y2-Y1)] \qquad (4)$$

$$\beta = \tan^{-1}[(X5-X6)/(Z5-Z6)] \qquad (5)$$

$$\gamma = \tan^{-1}[(X4-X3)/(Y4-Y3)] \qquad (6)$$

with the measurements for such calculations being obtained from the respective front, side and bottom views illustrated in FIG. 6. This knowledge of both the origin O' of the movable coordinate system and the three skew angles $\alpha$, $\beta$ and $\gamma$ fixes the absolute position of the movable light source 38 relative to the fixed coordinate system and housing 14. Fixed position reference points comprising, for example, point light sources 58 attached, for example, to the upper and lower edges of the mirror 46 are included, which light sources are energized to provide images 58I at the film 42. With the point light sources 58 at fixed known positions relative to the fixed reference frame, the images thereof provide reference points for the above-described measurements, as well as a scalability factor. The reference source lights may be connected to the power source 54 through the switch 56, or other switch, not shown, for the energization thereof.

Most present commercially available adjustable articulators are incapable of truly simulating individual jaw movements. Some articulators do include replaceable simulated mandibular condyles and associated maxillary cavities for simulating several "known" jaw movement characteristics. Obviously, an individual patient's jaw movements seldom correspond to any one of the movements which may be simulated. For setting most articulators, only knowledge of the extreme limit, or border, positions of the lateral and protrusive movements of the patient's jaws are required. Consequently, position and skew angle calculations of the above-described type involving equations (1) through (6) are made for the centric and end points of the recorded paths only. It will be apparent, then, that for many purposes, only such limit positions need be sensed and/or recorded.

It should be noted, however, that with the present arrangement a complete record of the movements is available and may be used. To facilitate the identity of path points which are simultaneously produced, the light source indicia may be simultaneously intermittently operated to provide broken-line traces of the jaw movements rather than the illustrated full-line traces obtained by continuous light source energization during jaw movements. As many calculations of position and skew angle as desired on each light trace may be performed for establishing the light source paths with the desired accuracy.

CALCULATION OF MANDIBULAR CONDYLE MOVEMENTS

The absolute positions of the indicia during jaw movements calculated as described above, together with measurements relating the patient's hinge axis to the recording device 10, are used in the calculation of the three-dimensional paths of the left and right mandibular condyles relative to the condyle positions with the patient's mandible is in centric position.

After the upper and lower clutches 26 and 28 have been fitted to the patient's teeth, measurements are made of the distances DL and DR (see FIG. 3) between a reference plane which passes perpendicularly through the movable arm 32 at the point it attaches to the clutch 28 and the patient's right and left hinge axis terminal points. Also, measurements of angles $\phi R$ and $\phi L$ (only $\phi R$ being shown in FIG. 2) between the lines DR and DL and the plane of the lower clutch extending through the point of attachment of the clutch to the arm 32 are obtained. Finally, the spacing D (FIG. 3) between the right and left terminal points of the patient's hinge axis is measured. The above-measurements, together with the above-described light source movement calculations and knowledge of physical dimensions of the recording device, provide necessary data for a mathematical solution of the patient's right and left mandibular condyle movements relative to centric position thereof.

Figure 7:
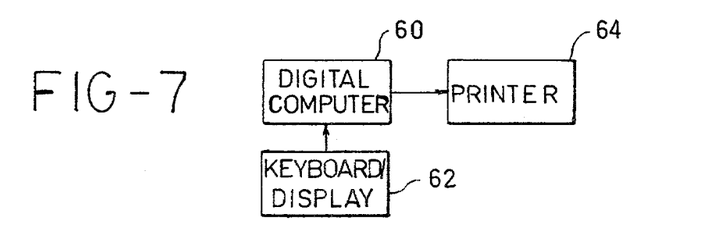
FIG. 7 is a block diagram showing means including a programmed digital computer for translating patient related measurements and jaw movement data into a mathematical model of mandibular condyle movements and articulator settings required to simulate such movements.

The calculations are easily performed by hand. However, to facilitate calculation of such mandibular condylar movements, a digital computer 60, seen in FIG. 7, with an associated terminal 62 comprising, for example, a keyboard/display unit, and a printer 64, may be employed. The above-described calculations of absolute positions of the light source means 38 during jaw movements together with the above-described hinge axis related measurements are supplied to the properly programmed digital computer 60 through the keyboard terminal 62 for calculation by the computer of the position vectors $\overrightarrow{DLO'}$ and $\overrightarrow{DRO'}$ from the origin O' of the moving reference frame to the left and right terminal hinge axes, respectively, of the patient. (see FIG. 3) These vectors are calculated relative to the fixed reference frame and, performing a Euler transform through the calculated angles $\alpha$, $\beta$ and $\gamma$, the end points of vectors $\overrightarrow{DLO}$ and $\overrightarrow{DRO}$ in the fixed reference frame are established, which end points comprise the locations of the left and right mandibular condyles. By performing these computations for many positions of the movable light source means 38, the locus of points is established which describes the absolute motion of mandibular condyles during recorded jaw movements. Such a record of condyle movements of the patient's mandible when the jaws are worked may be printed out at the printer 64 (FIG. 7). Obviously, other methods of mathematical solution are possible, including methods not involving Euler transformation.

Such mandibular condyle movement information is useful, of course, in determining settings of adjustments for dental articulators necessary to simulate the recorded jaw movements. Knowing the coordinate reference frame utilized in an articulator, and the calculated mandibular condyle path end points (or paths), it is a simple matter to program the digital computer 60 for calculation of adjustment settings required to "duplicate" such paths. Numerous different types of dental articulators are known and employed by dentists, which articulators utilize different adjustment schemes. The digital computer 60, therefor, preferably is programmed with different coordinate translation programs required for different type articulators. Such programming for coordinate transformation and articulator setting is well within the ability of artisans skilled in this art. Following is a typical computer printout which includes articulator settings for a DENAR D5-A type articulator.

---

CALCULATED ARTICULATOR SETTING

DOCTOR: HAMADA, JAMES H.
ADDRESS
PATIENT I.D.: XXX, XX, XXXX  DATE: XXXXXXXXX, XX, XXXX
POSTERIOR REFERENCE POINTS:  LEFT CONDYLE SPACING: 101.6 (MM.)
 RIGHT CONDYLE SPACING: 108 (MM.)
 LEFT CONDYLE ANGLE: 15 (DEGREES)
 RIGHT CONDYLE ANGLE: 12 (DEGREES)
TYPE OF ARTICULATOR: DENAR D5-A

-continued

| CALCULATED ARTICULATOR SETTING | | |
|---|---|---|
| POSTERIOR CONTROL: | LEFT FOSSA | RIGHT FOSSA |
| PROTRUSIVE PATH: | 30.0 DEGREES | 30.0 DEGREES |
| IMMEDIATE SIDE SLIP: | 1.0 MILLIMETERS | 0.5 MM. |
| PROGRESSIVE SIDE SLIP: | 10.0 DEGREES | 12.0 DEGREES |
| REAR WALL: | 15.0 DEGREES (FORE) | 23.0 DEGREES |
| VERTICAL AXIS: | 60.0 MILLIMETERS | 60.0 MM.(BACK) |
| TOP WALL: | 10.0 DEGREES (UP) | 5.0 DEGREES (UP) |

Although the method of this invention is believed to be clear a brief description of a typical use thereof with reference to the drawings now will be given. Clutches 26 and 28 are fitted to the teeth of the patient 12, and the hinge axis H (FIGS. 2 and 3) is located using conventional apparatus, not shown. Measurements are made of the distances DL and DR (FIG. 3) from the patient's left and right terminal hinge axes to the front of the lower clutch where the clutch attaches to the arm 32, and of the angles $\phi L$ and $\phi R$ (only $\phi R$ being shown in FIG. 2) between the plane of the lower clutch extending through the arm 32 and the lines DL and DR, respectively. Also, the horizontal spacing D (FIG. 3) between the left and right terminal hinge axes is measured. The clutches then are secured to recording device 10 for recording jaw movements.

Figure 5D:
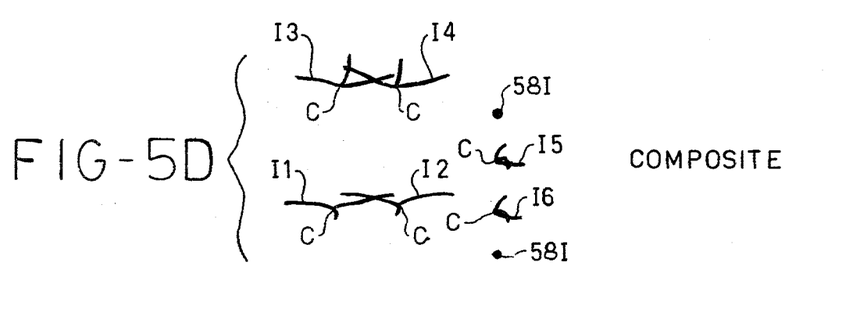

To record jaw movements, the patient places his jaws in centric position, the switch 56 is closed by the operator for energization of the light sources L1–L6, and the patient performs one of the jaw movements to be recorded i.e. a left lateral, right lateral, or protrusive jaw movement. At the completion of the movement the switch 56 is opened and the jaws are returned to centric position in preparation for recording another jaw movement. When all three movements have been recorded the negative film 42 is removed from the film pack 48 for developing and printing. A typical record is shown in FIG. 5D of the drawings except the traces would be white against a black background in the normal print of the negative.

The recording, together with the doctor's name, patient's identification number, type of articulator to be used, and the above-described measurements relating the recording device to the patient's hinge axis, are sent to a central location for computer conversion of the same to a printout which includes articulator settings required to duplicate the recorded jaw movements. Measurements at the end points of the recorded path of the light source means 38, as viewed from three directions, are made of the quantities X3, X4, X5, X6, Y1, Y2, Y3, Y4, Z1, Z2, Z5 and Z6 for the use in equations (1) through (6) to establish a plurality of points XO', YO' and ZO' and angles $\alpha$, $\beta$ and $\gamma$ of the light sources L1 through L6 relative to the fixed reference frame. (As noted above, measurements at a plurality of points along the recorded path may be made for use in determining the path of movement of the jaws, and not only the end points thereof.) This information, together with the above-mentioned hinge axis related measurements, are supplied to the digital computer 60 through terminal 62. The computer is programmed to convert such information into right and left mandibular condyle movements relative to centric position, which then are converted to articulator settings for the particular articulator to be used in duplicating such condyle movements. A printout of the type shown above with the necessary dental articulator settings is obtained from the printer 64, and a copy thereof is sent to the dentist for use in making the required articulator adjustments. Obviously, conversion to articulator settings without first determining right and left mandibular condyle movements, per se, is possible.

Figure 8:
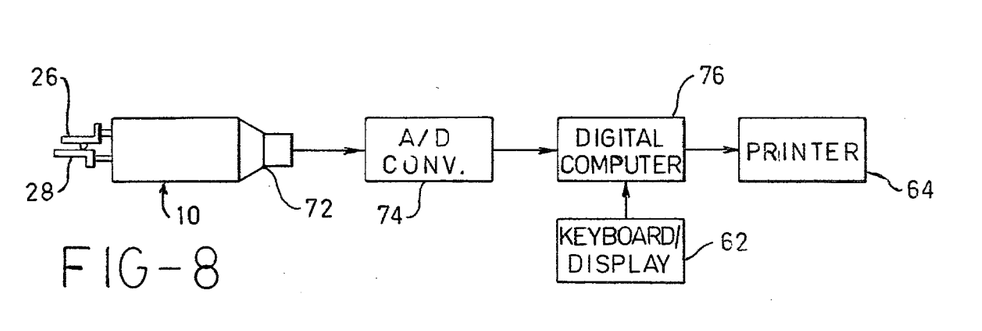
FIG. 8 is a diagrammatic showing of a modified form of this invention employing a video camera to view the light images and for supplying resultant jaw movement information to a digital computer.

The invention having been described in detail in accordance with the requirements of the Patent Statutes, various changes and modifications will suggest themselves to those skilled in the art. In FIG. 8, for example, there is shown an arrangement wherein the indicia of the recording device 10 are directed onto the face of a video camera 72 located at the image plane of the recording device instead of photographic negative film. The light traces are detected by the video camera as they are being produced, and the output from the camera is supplied to a digital computer 76 through a suitable interface 74 which includes an analog to digital converter. The computer is programmed to automatically perform the functions of determining position and skew angle of the light source pairs for the end points of the light paths (or for a plurality of points along the light image paths) and then to use such information in the calculation of mandibular condyle movements and/or articulator settings. Other pertinent data, including measurements relating the location of the patient's hinge axis to the recording device, are entered through use of keyboard 62 in the manner described above, and articulator settings are outputted by use of suitable means, such as printer 64. Of course, information concerning right and left mandibular condyle movements also may be obtained from the computer, if desired.

Figure 9:
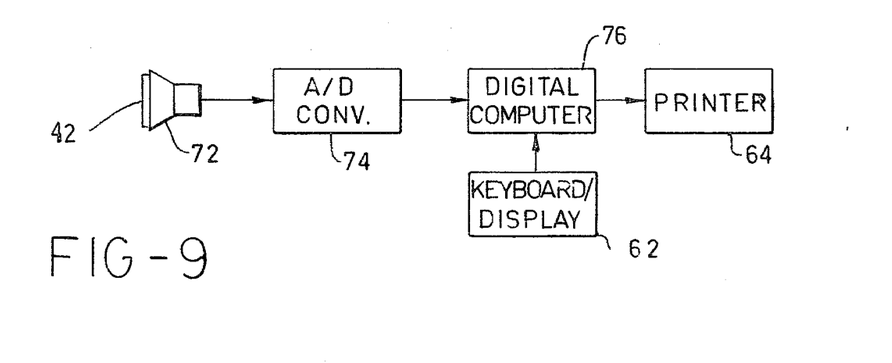
FIG. 9 is a diagrammatic showing of another modified form of this invention wherein a video camera is used to scan recorded light image traces produced by mandibular condyle movements.

Reference now is made to FIG. 9 wherein a system similar to that shown in FIG. 8 is illustrated. In the FIG. 9 arrangement the developed image 42 of the film exposed to the light tracings produced by the recording apparatus 10 is positioned in front of the video camera 72 for scanning thereof by the camera. (If desired, an optical system, not shown, may be located between the film and camera for projecting the images onto the camera face.) The remainder of the system corresponds to the arrangement illustrated in FIG. 8, described above, and requires no additional description. Obviously, a print of the negative 42 may be viewed by the camera, in place of the negative, if desired.

It will be apparent that the indicia-bearing arm may be directly viewed from three mutually orthogonal directions, rather than viewing mirror images of two pairs of the light sources by use of the mirrors 44 and 46. In such a case, light receiving and/or storage means, such as a focusing lens and film negative, would be included at each of the three viewing directions for the production of jaw movement records at three separate locations.

In the arrangement illustrated in FIGS. 1–4 the light source means 38 is shown as including six individual point light sources. If desired, a single lamp, or light source, could be mounted inside a suitably apertured housing through which apertures light from the single source would pass to provide the necessary point light sources. Also as noted above, means may be provided for identifying points on the light traces which are simultaneously produced during jaw movements. This may include means for modulating the power source for the light source means to simultaneously vary the brightness of the point light sources while recording. Additionally, radiation other than visible light may be used in the recording and/or sensing device 10 together with radiation receiving means responsive to such radiation.

Figure 10:
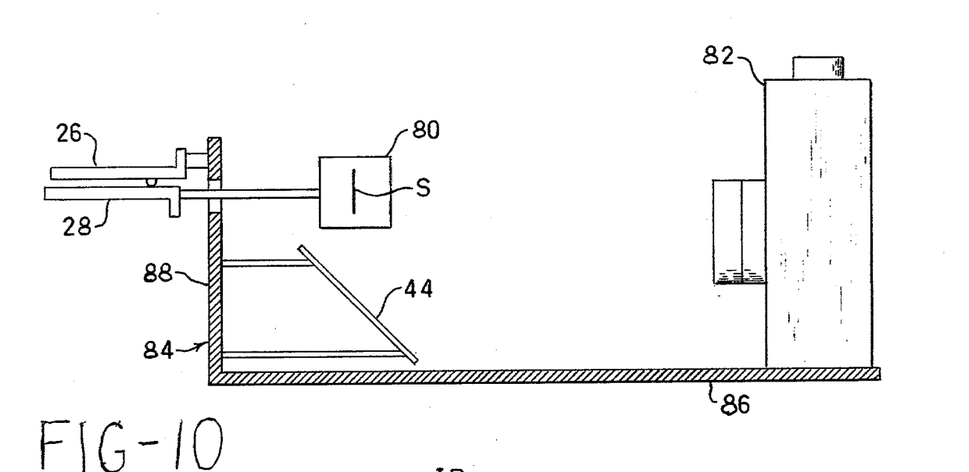
FIG. 10 is a longitudinal sectional view similar to that of FIG. 2 but showing a modified form of this invention employing indicia of a non-radiating type and a camera for recording the positions thereof with the jaws at their border positions.
Figure 11A:
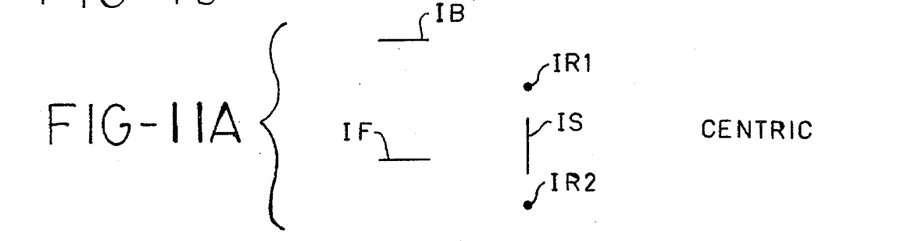
FIGS. 11A–11D show photographic images of the indicia included in the FIG. 10 arrangement.
Figure 11B:
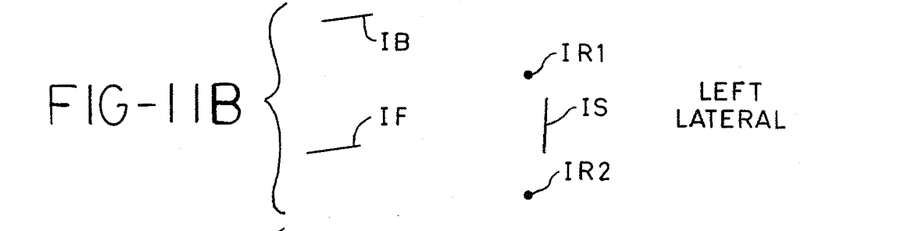
Figure 11C:
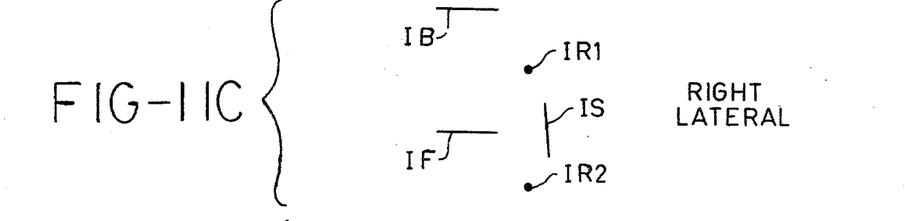
Figure 11D:
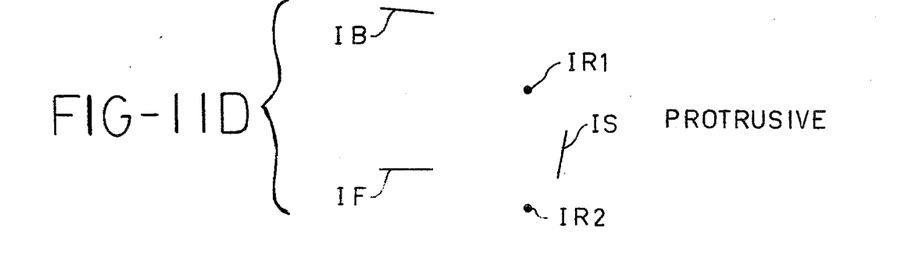

The use of indicia which are not light-emitting also is included within the scope of the present invention. In FIG. 10, to which reference now is made there is shown a recording apparatus which is similar to that shown in FIGS. 1-4 except that indicia in the form of line or bar members F, B, S (only line S at the side of block 80 at the inner free end of indicia-bearing arm 32 being shown). No light-tight housing is required since photographs of the indicia are made with the jaws in extreme limit positions, i.e. in centric, right lateral, left lateral and protrusive positions, by use of camera 82. A frame 84 comprising a base 86 and upright 88 supports the camera 82 and upper clutch 26. The lower clutch 28 and attached indicia-bearing arm 32 are free to move in any direction. The front indicium F (not shown) is directly viewable by the camera 82 whereas the bottom and side indicia B and S (only indicium S being shown) are viewable through the mirrors 44 and 46, respectively (only bottom mirror 44 being shown in FIG. 10).

In FIGS. 11A through 11D images of the indicia with the jaws in centric, left lateral, right lateral and protrusive positions, respectively, are shown. Also, images IR1 and IR2 of suitable reference points R1 and R2 viewable adjacent the image IS of the side-facing indicia S are shown in each of these Figures. The block 80 and other structure viewable by the camera lense system are not shown in FIGS. 11A-11D to avoid confusion. As with the point light sources, the midpoint of the ends of the individual indicia identify the origin O' of the movable reference frame, and markings (not shown) identifying such midpoints may be included on the block. The angles between the fixed and movable reference frames are calculated in the same manner described above in the case of point light sources. In the FIG. 10 and 11 arrangement photographs with the jaws in only the extreme limit positions are made which provide sufficient data for the computation of articulator settings.

Other changes and modifications include the use of line light sources similar to the indicia F, S, B shown in FIG. 10, in place of the point light sources employed in the FIG. 1-4 arrangement. Also, the indicia-bearing member may include a single point light source together with suitable light-receiving means such as arrays of photooptic receiving devices for sensing movement in three mutually orthogonal planes spaced therefrom. Alternatively, holographic techniques may be used for encoding position data provided by a single omnidirectional point light carried by the movable indicia-bearing member. It is intended that the above and other such changes and modifications shall fall within the spirit and scope of the invention as defined in the appended claims.

What is claimed is:

1. Dental apparatus for use in obtaining jaw movement information comprising,
    relatively movable indicia-bearing and light responsive means,
    image-forming means for providing images of indicia at said indicia-bearing means on said light responsive means, and
    means for attaching said indicia-bearing and light responsive means to a patient's jaws to provide jaw position data at said light responsive means upon relative movement of the patient's jaws and attached indicia-bearing and light responsive means.

2. Dental apparatus as defined in claim 1 wherein said indicia comprise points.

3. Dental apparatus as defined in claim 1 wherein said indicia comprises lines.

4. Dental apparatus as defined in claim 1 wherein,
    said attaching means includes first and second clutches secured to said respective, indicia-bearing and light responsive means and attachable to said patient's mandibular and maxillary teeth, respectively.

5. Dental apparatus as defined in claim 1 wherein said light responsive means comprises photographic negative film.

6. Dental apparatus as defined in claim 1 wherein said light responsive means comprises a video camera.

7. Dental apparatus as defined in claim 1 wherein said indicia comprise first, second and third pairs of points spaced from the origin of a movable reference frame and arranged to be viewed by said light responsive means from along three mutually orthogonal axes of the movable reference frame.

8. Dental apparatus as defined in claim 7 wherein said indicia comprise point light sources.

9. Dental apparatus as defined in claim 7 including first and second mirrors for viewing said second and third pairs of points on said indicia-bearing means.

10. Dental apparatus as defined in claim 1 including,
    an enclosure to which said light responsive means is attached,
    a movable arm extending through an aperture in a wall of said enclosure to which said indicia-bearing means is attached at the inner end of said arm,
    said attaching means comprising clutches secured to the outer end of said movable arm and enclosure, and attachable to said patient's mandibular and maxillary teeth, respectively.

11. A method of obtaining and utilizing jaw movement information for dental use comprising,
    providing first and second clutches coupled to relatively movable signal receiving means and signal source means, respectively,
    securing the clutches to the patient's jaws,
    energizing the signal source means while moving the patient's mandibular to provide an analog record at said signal receiving means related to said mandibular movement,
    converting said analog record to digital information form for digital computer use,
    entering said digital information into a digital computer programmed to calculate left and right mandibular condyle movement therefrom.

12. The method as defined in claim 11 including,
    using said calculated left and right mandibular condyle movements, calculating by said computer articulator settings required to simulate the jaw movement.

13. A method of obtaining articulator settings for adjusting a dental articulator to simulate a patient's mandibular movement comprising, obtaining an analog signal representation dependent upon the patient's mandibular movements, converting the analog signal representation into digital electronic signal form, and using said digital electronic signals to calculate articulator settings required for adjusting a dental articulator to simulate the patient's mandibular movement.

14. The method as defined in claim 13 wherein said analog signal representation is obtained by focusing light from a plurality of point light sources attached to the patient's mandibular teeth onto light-sensing means attached to the patient's maxillary teeth at different relative positions of the patient's jaws.

15. The method as defined in claim 14 wherein said light-sensing means comprises photographic negative film exposed to said point light sources during mandicular movement by the patient.

16. The method as defined in claim 15 wherein said light-sensing means comprises a video camera exposed to said point light sources during mandibular movement by the patient.

17. The method as defined in claim 13 wherein said analog signal representation is obtained by forming images of indicia carried by indicia-bearing means attached to the patient's mandibular teeth onto light-responsive means attached to the patient's maxillary teeth at different relative positions of the patient's jaws.

18. Apparatus for condylar position-sensing of the mandibular joints of a patient when the patient's jaws are worked, said apparatus including, a stationary housing, movable indicia-supporting means extending into the housing, indicia carried by said indicia-supporting means inside said housing, first and second clutches for securing the outer end of the indicia-supporting means to the mandibular teeth of the patient and the stationary housing to maxillary teeth of the patient, respectively, light responsive means attached to said housing, and means for forming images of said indicia on said light responsive means for sensing three-dimensional positional and angular displacement of said indicia-supporting means relative to said housing with condylar movements of the patient's mandible.

19. Apparatus for condylar position-sensing as defined in claim 18 wherein, said indicia comprise first, second and third pairs of point light sources equally spaced from a point comprising the origin of a movable reference frame having three, mutually orthogonal axes fixed relative to the indicia-supporting means, said first, second and third point light sources being arranged on said indicia-supporting means for directing light along said three axes, respectively.

20. Apparatus for condylar position-sensing as defined in claim 19 including, first and second mirrors inside said housing for reflecting light from said first and second pairs of said point light sources onto said light responsive means through said image forming means.

21. Apparatus for condylar position-sensing as defined in claim 19 wherein said light responsive means comprises a photographic negative film.

* * * * *